US008150499B2

(12) United States Patent
Gelbart et al.

(10) Patent No.: US 8,150,499 B2
(45) Date of Patent: Apr. 3, 2012

(54) AUTOMATIC ATHERECTOMY SYSTEM

(75) Inventors: Daniel Gelbart, Vancouver (CA);
Samuel Victor Lichtenstein, Vancouver (CA)

(73) Assignee: Kardium Inc., Vancouver (CA)

( * ) Notice: Subject to any disclaimer, the term of this patent is extended or adjusted under 35 U.S.C. 154(b) by 0 days.

(21) Appl. No.: 12/950,871

(22) Filed: Nov. 19, 2010

(65) Prior Publication Data

US 2011/0125172 A1    May 26, 2011

Related U.S. Application Data

(62) Division of application No. 11/436,584, filed on May 19, 2006, now abandoned.

(51) Int. Cl.
*A61B 5/05* (2006.01)
(52) U.S. Cl. ...................................... 600/427
(58) Field of Classification Search .............. 606/219, 606/159, 170–171, 1, 79, 80, 96; 600/427, 600/471, 546–547, 587; 604/22, 27, 35, 604/508; 700/253, 258
See application file for complete search history.

(56) References Cited

U.S. PATENT DOCUMENTS

| 4,114,202 | A |   | 9/1978 | Roy et al. ........................... 3/1.5 |
| 4,164,046 | A |   | 8/1979 | Cooley ................................ 3/1.5 |
| 4,225,148 | A | * | 9/1980 | Andersson ............. 280/124.146 |
| 4,240,441 | A |   | 12/1980 | Khalil ............................ 128/692 |
| 4,263,680 | A |   | 4/1981 | Reul et al. ......................... 3/1.5 |
| 4,273,128 | A | * | 6/1981 | Lary ............................... 606/159 |
| 4,411,266 | A |   | 10/1983 | Cosman .................... 128/303.18 |
| 4,490,859 | A |   | 1/1985 | Black et al. ......................... 3/1.5 |
| 4,543,090 | A | * | 9/1985 | McCoy ....................... 604/95.05 |
| 4,770,187 | A |   | 9/1988 | Lash et al. ..................... 128/760 |
| 4,794,912 | A |   | 1/1989 | Lia ..................................... 128/4 |
| 4,850,957 | A | * | 7/1989 | Summers ......................... 604/22 |
| 4,887,613 | A | * | 12/1989 | Farr et al. ....................... 606/159 |
| 4,890,602 | A |   | 1/1990 | Hake ................................. 128/4 |
| 4,890,612 | A |   | 1/1990 | Kensey .......................... 606/213 |
| 4,893,613 | A |   | 1/1990 | Hake ................................. 128/4 |

(Continued)

FOREIGN PATENT DOCUMENTS

EP           0723467         4/2002

(Continued)

OTHER PUBLICATIONS

Becker, R. et al., "Ablation of Atrial Fibrillation: Energy Sources and Navigation Tools: A Review," *Journal of Electrocardiology*, 37(Supplement 2004):55-62, 2004.

(Continued)

*Primary Examiner* — Melanie Tyson
*Assistant Examiner* — Son Dang
(74) *Attorney, Agent, or Firm* — Seed IP Law Group PLLC (57) ABSTRACT

An automatic atherectomy system uses a rotary burr at the tip of a catheter as a sensing device, in order to measure both electrical conductivity and permittivity of surrounding tissue at multiple frequencies. From these parameters it is determined which tissue lies in different directions around the tip. A servo system steers the catheter tip in the direction of the tissue to be removed. In non-atherectomy applications the rotary burr can be replaced with any desired tool and the system can be used to automatically steer the catheter to the desired position. The steering may be done hydraulically, by pressurizing miniature bellows located near the catheter tip.

9 Claims, 7 Drawing Sheets

U.S. PATENT DOCUMENTS

| | | | | |
|---|---|---|---|---|
| 4,895,166 | A * | 1/1990 | Farr et al. | 600/564 |
| 4,921,499 | A | 5/1990 | Hoffman et al. | 623/16 |
| 4,942,788 | A * | 7/1990 | Farr et al. | 76/115 |
| 4,979,514 | A | 12/1990 | Sekii et al. | 128/713 |
| 4,998,933 | A * | 3/1991 | Eggers et al. | 606/41 |
| 5,026,384 | A * | 6/1991 | Farr et al. | 606/159 |
| 5,047,047 | A | 9/1991 | Yoon | 606/216 |
| 5,122,137 | A * | 6/1992 | Lennox | 606/40 |
| 5,127,902 | A * | 7/1992 | Fischell | 604/22 |
| 5,156,151 | A | 10/1992 | Imran | 128/642 |
| 5,174,299 | A | 12/1992 | Nelson | 128/692 |
| 5,176,693 | A * | 1/1993 | Pannek, Jr. | 606/159 |
| 5,178,620 | A | 1/1993 | Eggers et al. | 606/41 |
| 5,192,291 | A * | 3/1993 | Pannek, Jr. | 606/159 |
| 5,201,316 | A * | 4/1993 | Pomeranz et al. | 600/463 |
| 5,228,442 | A | 7/1993 | Imran | 128/642 |
| 5,242,386 | A | 9/1993 | Holzer | 604/22 |
| 5,279,299 | A | 1/1994 | Imran | 128/642 |
| 5,293,869 | A | 3/1994 | Edwards et al. | 128/642 |
| 5,312,435 | A | 5/1994 | Nash et al. | 606/213 |
| 5,317,952 | A * | 6/1994 | Immega | 91/418 |
| 5,341,807 | A | 8/1994 | Nardella | 128/642 |
| 5,366,443 | A | 11/1994 | Eggers et al. | 604/114 |
| 5,379,773 | A | 1/1995 | Hornsby | 128/662.06 |
| 5,419,767 | A * | 5/1995 | Eggers et al. | 604/114 |
| 5,450,860 | A | 9/1995 | O'Connor | 128/898 |
| 5,478,353 | A | 12/1995 | Yoon | 606/213 |
| 5,496,267 | A * | 3/1996 | Drasler et al. | 604/22 |
| 5,531,760 | A | 7/1996 | Alwafaie | 606/216 |
| 5,557,967 | A | 9/1996 | Renger | 73/204.24 |
| 5,593,424 | A | 1/1997 | Northrup, III | 606/232 |
| 5,598,848 | A | 2/1997 | Swanson et al. | 128/696 |
| 5,662,587 | A * | 9/1997 | Grundfest et al. | 600/114 |
| 5,681,308 | A | 10/1997 | Edwards et al. | 606/41 |
| 5,681,336 | A * | 10/1997 | Clement et al. | 606/159 |
| 5,687,723 | A | 11/1997 | Avitall | 128/642 |
| 5,697,285 | A * | 12/1997 | Nappi et al. | 91/519 |
| 5,713,896 | A * | 2/1998 | Nardella | 606/50 |
| 5,716,397 | A | 2/1998 | Myers | 623/2 |
| 5,720,726 | A | 2/1998 | Marcadis et al. | 604/96 |
| 5,728,114 | A | 3/1998 | Evans et al. | 606/148 |
| 5,730,127 | A | 3/1998 | Avitall | 128/642 |
| 5,762,066 | A | 6/1998 | Law et al. | 128/660.03 |
| 5,769,846 | A | 6/1998 | Edwards et al. | 606/41 |
| 5,782,239 | A | 7/1998 | Webster, Jr. | 128/642 |
| 5,782,879 | A | 7/1998 | Rosborough et al. | 607/6 |
| 5,800,495 | A | 9/1998 | Machek et al. | 607/116 |
| 5,824,066 | A | 10/1998 | Gross | 623/2 |
| 5,836,990 | A | 11/1998 | Li | 607/28 |
| 5,876,343 | A | 3/1999 | Teo | 600/443 |
| 5,881,727 | A | 3/1999 | Edwards | 128/642 |
| 5,891,136 | A | 4/1999 | McGee et al. | 606/41 |
| 5,904,711 | A | 5/1999 | Flom et al. | 607/129 |
| 5,919,207 | A | 7/1999 | Taheri | 606/219 |
| 5,921,924 | A | 7/1999 | Avitall | 600/374 |
| 5,935,075 | A * | 8/1999 | Casscells et al. | 600/474 |
| 5,961,440 | A | 10/1999 | Schweich, Jr. et al. | 600/16 |
| 5,984,950 | A | 11/1999 | Cragg et al. | 606/216 |
| 6,001,069 | A * | 12/1999 | Tachibana et al. | 601/2 |
| 6,104,944 | A | 8/2000 | Martinelli | 600/424 |
| 6,138,043 | A | 10/2000 | Avitall | 600/377 |
| 6,142,993 | A | 11/2000 | Whayne et al. | 606/41 |
| 6,156,046 | A * | 12/2000 | Passafaro et al. | 606/159 |
| 6,210,432 | B1 | 4/2001 | Solem et al. | 623/1.15 |
| 6,217,573 | B1 | 4/2001 | Webster | 606/41 |
| 6,241,747 | B1 | 6/2001 | Ruff | 606/216 |
| 6,248,124 | B1 | 6/2001 | Pedros et al. | 606/213 |
| 6,258,258 | B1 | 7/2001 | Sartori et al. | 208/263 |
| 6,266,550 | B1 * | 7/2001 | Selmon et al. | 600/407 |
| 6,304,769 | B1 | 10/2001 | Arenson et al. | 600/424 |
| 6,306,135 | B1 | 10/2001 | Ellman et al. | 606/45 |
| 6,308,091 | B1 | 10/2001 | Avitall | 600/374 |
| 6,346,105 | B1 | 2/2002 | Tu et al. | 606/41 |
| 6,358,258 | B1 | 3/2002 | Arcia et al. | 606/139 |
| 6,383,151 | B1 | 5/2002 | Diederich et al. | 601/2 |
| 6,389,311 | B1 | 5/2002 | Whayne et al. | 600/523 |
| 6,391,048 | B1 | 5/2002 | Ginn et al. | 606/213 |
| 6,391,054 | B2 | 5/2002 | Carpentier et al. | 623/2.37 |
| 6,402,781 | B1 | 6/2002 | Langberg et al. | 623/2.36 |
| 6,436,052 | B1 | 8/2002 | Nikolic et al. | 600/529 |
| 6,475,223 | B1 | 11/2002 | Werp et al. | 606/108 |
| 6,485,409 | B1 * | 11/2002 | Voloshin et al. | 600/115 |
| 6,485,489 | B2 | 11/2002 | Teirstein et al. | 606/41 |
| 6,506,210 | B1 | 1/2003 | Kanner | 606/213 |
| 6,514,249 | B1 | 2/2003 | Maguire et al. | 606/41 |
| 6,529,756 | B1 | 3/2003 | Phan et al. | 600/374 |
| 6,537,198 | B1 | 3/2003 | Vidlund et al. | 600/16 |
| 6,537,314 | B2 | 3/2003 | Langberg et al. | 623/2.36 |
| 6,540,670 | B1 | 4/2003 | Hirata et al. | 600/152 |
| 6,551,312 | B2 | 4/2003 | Zhang et al. | 606/41 |
| 6,569,160 | B1 | 5/2003 | Goldin et al. | 606/41 |
| 6,569,198 | B1 | 5/2003 | Wilson et al. | 623/2.37 |
| 6,575,971 | B2 | 6/2003 | Hauck et al. | 606/52 |
| 6,589,208 | B2 | 7/2003 | Ewers et al. | 604/104 |
| 6,626,930 | B1 | 9/2003 | Allen et al. | 606/213 |
| 6,632,238 | B2 | 10/2003 | Ginn et al. | 606/213 |
| 6,662,034 | B2 | 12/2003 | Segner et al. | 600/373 |
| 6,704,590 | B2 | 3/2004 | Haldeman | 600/407 |
| 6,723,038 | B1 | 4/2004 | Schroeder et al. | 600/16 |
| 6,726,716 | B2 | 4/2004 | Marquez | 623/2.36 |
| 6,760,616 | B2 | 7/2004 | Hoey et al. | 600/547 |
| 6,780,197 | B2 | 8/2004 | Roe et al. | 606/213 |
| 6,797,001 | B2 | 9/2004 | Mathis et al. | 623/2.37 |
| 6,800,090 | B2 | 10/2004 | Alferness et al. | 623/2.36 |
| 6,837,886 | B2 | 1/2005 | Collins et al. | 606/41 |
| 6,852,076 | B2 | 2/2005 | Nikolic et al. | 600/37 |
| 6,855,143 | B2 | 2/2005 | Davison et al. | 606/41 |
| 6,890,353 | B2 | 5/2005 | Cohn et al. | 623/2.37 |
| 6,892,091 | B1 | 5/2005 | Ben-Haim et al. | 600/509 |
| 6,899,674 | B2 | 5/2005 | Viebach et al. | 600/152 |
| 6,907,297 | B2 | 6/2005 | Wellman et al. | 607/122 |
| 6,908,478 | B2 | 6/2005 | Alferness et al. | 623/1.11 |
| 6,913,576 | B2 | 7/2005 | Bowman | 606/505 |
| 6,918,903 | B2 | 7/2005 | Bass | 604/511 |
| 6,926,669 | B1 | 8/2005 | Stewart et al. | 600/439 |
| 6,942,657 | B2 | 9/2005 | Sinofsky et al. | 606/15 |
| 6,949,122 | B2 | 9/2005 | Adams et al. | 623/2.36 |
| 6,960,229 | B2 | 11/2005 | Mathis et al. | 623/2.36 |
| 6,986,775 | B2 | 1/2006 | Morales et al. | 606/139 |
| 6,989,010 | B2 | 1/2006 | Francischelli et al. | 606/42 |
| 6,989,028 | B2 | 1/2006 | Lashinski et al. | 623/2.37 |
| 6,994,093 | B2 | 2/2006 | Murphy et al. | 128/898 |
| 6,997,951 | B2 | 2/2006 | Solem et al. | 623/2.37 |
| 7,001,383 | B2 | 2/2006 | Keidar | 606/41 |
| 7,025,776 | B1 | 4/2006 | Houser et al. | 606/213 |
| 7,050,848 | B2 | 5/2006 | Hoey et al. | 600/547 |
| 7,052,487 | B2 | 5/2006 | Cohn et al. | 604/509 |
| 7,068,867 | B2 | 6/2006 | Adoram et al. | 385/12 |
| 7,141,019 | B2 | 11/2006 | Pearlman | 600/437 |
| 7,144,363 | B2 | 12/2006 | Pai et al. | 600/167 |
| 7,177,677 | B2 | 2/2007 | Kaula et al. | 600/546 |
| 7,186,210 | B2 | 3/2007 | Feld et al. | 600/16 |
| 7,187,964 | B2 | 3/2007 | Khoury | 600/509 |
| 7,189,202 | B2 | 3/2007 | Lau et al. | 600/37 |
| 7,279,007 | B2 | 10/2007 | Nikolic et al. | 623/11.11 |
| 7,300,435 | B2 | 11/2007 | Wham et al. | 606/34 |
| 7,303,526 | B2 | 12/2007 | Sharkey et al. | 600/37 |
| 7,335,196 | B2 | 2/2008 | Swanson et al. | 606/41 |
| 7,507,252 | B2 | 3/2009 | Lashinski et al. | 623/2.37 |
| 7,738,967 | B2 | 6/2010 | Salo | 607/116 |
| 2001/0003158 | A1 | 6/2001 | Kensey et al. | 606/213 |
| 2001/0005787 | A1 | 6/2001 | Oz et al. | 606/142 |
| 2001/0018611 | A1 | 8/2001 | Solem et al. | 623/2.37 |
| 2001/0020126 | A1* | 9/2001 | Swanson et al. | 600/407 |
| 2002/0002329 | A1 | 1/2002 | Avitall | 600/377 |
| 2002/0016628 | A1 | 2/2002 | Langberg et al. | 623/2.36 |
| 2002/0087156 | A1 | 7/2002 | Maguire et al. | 606/41 |
| 2002/0087173 | A1 | 7/2002 | Alferness et al. | 606/151 |
| 2002/0107478 | A1* | 8/2002 | Wendlandt | 604/95.01 |
| 2002/0107511 | A1 | 8/2002 | Collins et al. | 606/41 |
| 2002/0115944 | A1 | 8/2002 | Mendes et al. | 600/594 |
| 2002/0169504 | A1 | 11/2002 | Alferness et al. | 623/2.36 |
| 2002/0177782 | A1* | 11/2002 | Penner | 600/485 |
| 2002/0183836 | A1 | 12/2002 | Liddicoat et al. | 623/2.11 |
| 2002/0183841 | A1 | 12/2002 | Cohn et al. | 623/2.36 |
| 2002/0188170 | A1 | 12/2002 | Santamore et al. | 600/37 |
| 2003/0050685 | A1 | 3/2003 | Nikolic et al. | 623/1.11 |

| | | | | | | | |
|---|---|---|---|---|---|---|---|
| 2003/0069570 A1 | 4/2003 | Witzel et al. .................. 606/28 | | 2007/0198058 A1 | 8/2007 | Gelbart et al. ................ 606/213 |
| 2003/0069636 A1 | 4/2003 | Solem et al. ................. 623/2.37 | | 2007/0213578 A1 | 9/2007 | Khairkhanan et al. .......... 600/16 |
| 2003/0078465 A1 | 4/2003 | Pai et al. ......................... 600/16 | | 2007/0213815 A1 | 9/2007 | Khairkhanan et al. ......... 623/3.1 |
| 2003/0078671 A1 | 4/2003 | Lesniak et al. ............. 623/23.64 | | 2007/0249999 A1* | 10/2007 | Sklar et al. ............... 604/101.05 |
| 2003/0105384 A1 | 6/2003 | Sharkey et al. ................. 600/16 | | 2007/0270688 A1 | 11/2007 | Gelbart et al. ................. 600/427 |
| 2003/0105520 A1 | 6/2003 | Alferness et al. ............. 623/2.36 | | 2007/0299343 A1 | 12/2007 | Waters ......................... 600/443 |
| 2003/0109770 A1 | 6/2003 | Sharkey et al. ................. 600/16 | | 2008/0004534 A1 | 1/2008 | Gelbart et al. ................. 600/508 |
| 2003/0181819 A1 | 9/2003 | Desai ........................... 600/510 | | 2008/0004643 A1* | 1/2008 | To et al. ........................ 606/159 |
| 2003/0229395 A1 | 12/2003 | Cox ............................. 623/2.36 | | 2008/0004697 A1 | 1/2008 | Lichtenstein et al. ........ 623/2.11 |
| 2004/0002626 A1 | 1/2004 | Feld et al. ....................... 600/37 | | 2008/0045778 A1 | 2/2008 | Lichtenstein et al. .......... 600/16 |
| 2004/0054279 A1 | 3/2004 | Hanley .......................... 600/424 | | 2008/0071298 A1 | 3/2008 | Khairkhanan et al. ........ 606/151 |
| 2004/0133273 A1 | 7/2004 | Cox ............................. 623/2.11 | | 2008/0312713 A1 | 12/2008 | Wilfley et al. ................... 607/41 |
| 2004/0138744 A1 | 7/2004 | Lashinski et al. ............. 623/2.36 | | 2009/0131930 A1 | 5/2009 | Gelbart et al. ................... 606/41 |
| 2004/0153146 A1 | 8/2004 | Lashinski et al. ............. 623/2.36 | | 2009/0157058 A1* | 6/2009 | Ferren et al. ................ 604/891.1 |
| 2004/0158321 A1 | 8/2004 | Reuter et al. ................. 623/2.36 | | 2009/0192441 A1 | 7/2009 | Gelbart et al. ................... 604/22 |
| 2004/0176797 A1 | 9/2004 | Opolski ........................ 606/213 | | 2009/0287304 A1 | 11/2009 | Dahlgren et al. ............ 623/2.37 |
| 2004/0186566 A1 | 9/2004 | Hindrichs et al. ........... 623/2.37 | | | | |
| 2004/0215232 A1 | 10/2004 | Belhe et al. .................. 606/213 | | FOREIGN PATENT DOCUMENTS | | |
| 2004/0243170 A1 | 12/2004 | Suresh et al. ................. 606/198 | | WO | 95/10320 | 4/1995 |
| 2004/0249408 A1 | 12/2004 | Murphy et al. ............... 606/198 | | WO | 03/015611 | 2/2003 |
| 2004/0249453 A1 | 12/2004 | Cartledge et al. ............. 623/2.37 | | WO | 03/077800 | 9/2003 |
| 2004/0267358 A1 | 12/2004 | Reitan .......................... 623/2.37 | | WO | 2004/012629 | 2/2004 |
| 2005/0004668 A1 | 1/2005 | Aklog et al. ................. 623/2.36 | | WO | 2004/047679 | 6/2004 |
| 2005/0015109 A1 | 1/2005 | Lichtenstein ................. 606/200 | | WO | 2004/084746 | 10/2004 |
| 2005/0054938 A1 | 3/2005 | Wehman et al. ............. 600/483 | | WO | 2004/100803 | 11/2004 |
| 2005/0055089 A1 | 3/2005 | Macoviak et al. ............ 623/2.37 | | WO | 2005/070330 | 8/2005 |
| 2005/0060030 A1 | 3/2005 | Lashinski et al. ............ 623/2.37 | | WO | 2005/102181 | 11/2005 |
| 2005/0064665 A1 | 3/2005 | Han .............................. 438/286 | | WO | 2006/017809 | 2/2006 |
| 2005/0065420 A1 | 3/2005 | Collins et al. ................ 600/374 | | WO | 2006/105121 | 10/2006 |
| 2005/0065504 A1 | 3/2005 | Melsky et al. .................. 606/16 | | WO | 2006/135747 | 12/2006 |
| 2005/0080402 A1 | 4/2005 | Santamore et al. .............. 606/1 | | WO | 2006/135749 | 12/2006 |
| 2005/0096647 A1* | 5/2005 | Steinke et al. .................. 606/41 | | WO | 2007/021647 | 2/2007 |
| 2005/0107723 A1 | 5/2005 | Wehman et al. ............. 600/595 | | WO | 2007/115390 | 10/2007 |
| 2005/0107871 A1 | 5/2005 | Realyvasquez et al. ...... 623/2.11 | | WO | 2008/002606 | 1/2008 |
| 2005/0125030 A1 | 6/2005 | Forsberg et al. ............. 606/213 | | WO | 2009/065042 | 5/2009 |
| 2005/0148892 A1 | 7/2005 | Desai ........................... 600/510 | | | | |
| 2005/0149014 A1 | 7/2005 | Hauck et al. .................... 606/41 | | OTHER PUBLICATIONS | | |
| 2005/0154252 A1 | 7/2005 | Sharkey et al. ................. 600/37 | | | | |
| 2005/0182365 A1 | 8/2005 | Hennemann et al. ......... 604/113 | | | | |
| 2005/0187620 A1 | 8/2005 | Pai et al. ....................... 623/2.37 | | | | |
| 2005/0197692 A1 | 9/2005 | Pai et al. ........................ 623/2.1 | | | | |
| 2005/0197693 A1 | 9/2005 | Pai et al. ........................ 623/2.1 | | | | |
| 2005/0197694 A1 | 9/2005 | Pai et al. ........................ 623/2.1 | | | | |
| 2005/0203558 A1* | 9/2005 | Maschke ....................... 606/180 | | | | |
| 2005/0209636 A1 | 9/2005 | Widomski et al. ............ 606/213 | | | | |
| 2005/0216054 A1 | 9/2005 | Widomski et al. ............ 606/213 | | | | |
| 2005/0240249 A1 | 10/2005 | Tu et al. .......................... 607/96 | | | | |
| 2005/0251116 A1* | 11/2005 | Steinke et al. .................... 606/8 | | | | |
| 2005/0251132 A1 | 11/2005 | Oral et al. ........................ 606/41 | | | | |
| 2005/0256521 A1 | 11/2005 | Kozel .............................. 606/41 | | | | |
| 2005/0267574 A1 | 12/2005 | Cohn et al. ................... 623/2.36 | | | | |
| 2006/0009755 A1 | 1/2006 | Sra ................................. 606/32 | | | | |
| 2006/0009756 A1 | 1/2006 | Francischelli et al. .......... 606/32 | | | | |
| 2006/0014998 A1 | 1/2006 | Sharkey et al. ................. 600/16 | | | | |
| 2006/0015002 A1 | 1/2006 | Moaddeb et al. ............... 600/37 | | | | |
| 2006/0015003 A1 | 1/2006 | Moaddes et al. ................ 600/37 | | | | |
| 2006/0015038 A1 | 1/2006 | Weymarn-Scharli ......... 600/585 | | | | |
| 2006/0015096 A1* | 1/2006 | Hauck et al. .................... 606/41 | | | | |
| 2006/0025800 A1 | 2/2006 | Suresh .......................... 606/198 | | | | |
| 2006/0030881 A1 | 2/2006 | Sharkey et al. ............... 606/213 | | | | |
| 2006/0085049 A1 | 4/2006 | Cory et al. ....................... 607/48 | | | | |
| 2006/0135968 A1 | 6/2006 | Schaller ........................ 606/144 | | | | |
| 2006/0135970 A1 | 6/2006 | Schaller ........................ 606/152 | | | | |
| 2006/0184242 A1 | 8/2006 | Lichtenstein ................. 623/2.37 | | | | |
| 2006/0199995 A1 | 9/2006 | Vijay ............................... 600/37 | | | | |
| 2006/0229491 A1 | 10/2006 | Sharkey et al. ................. 600/37 | | | | |
| 2006/0235286 A1 | 10/2006 | Stone et al. ................... 600/381 | | | | |
| 2006/0235314 A1 | 10/2006 | Migliuolo et al. ............ 600/505 | | | | |
| 2006/0264980 A1 | 11/2006 | Khairkhahan et al. ........ 606/153 | | | | |
| 2006/0281965 A1 | 12/2006 | Khairkhahan et al. .......... 600/37 | | | | |
| 2006/0293698 A1 | 12/2006 | Douk ............................ 606/142 | | | | |
| 2006/0293725 A1 | 12/2006 | Rubinsky et al. ............... 607/72 | | | | |
| 2007/0016068 A1* | 1/2007 | Grunwald et al. ............ 600/468 | | | | |
| 2007/0038208 A1 | 2/2007 | Kefer .............................. 606/34 | | | | |
| 2007/0088362 A1* | 4/2007 | Bonutti et al. ................... 606/99 | | | | |
| 2007/0115390 A1 | 5/2007 | Makara et al. ................ 348/552 | | | | |
| 2007/0118215 A1 | 5/2007 | Moaddeb ...................... 623/2.37 | | | | |
| 2007/0129717 A1 | 6/2007 | Brown, III et al. .............. 606/41 | | | | |
| 2007/0161846 A1 | 7/2007 | Nikolic et al. .................. 600/16 | | | | |

Buchbinder, Maurice, MD, "Dynamic Mitral Valve Annuloplasty: A Reshapable Ring for Residual and Recurring MR," from the *Foundation for Cardiovascular Medicine*, La Jolla, CA. May 24, 2007.

Calkins, Hugh, "Radiofrequency Catheter Ablation of Supraventricular Arrhythmias," *Heart*, 85:594-600, 2001.

De Ponti et al., "Non-Fluoroscopic Mapping Systems for Electrophysiology: The 'Tool or Toy' Dilemma After 10 Years," European Heart Journal 27:1134-1136, 2006.

Konings et al., "Development of an Intravascular Impedance Catheter for Detection of Fatty Lesions in Arteries," *IEEE Transactions on Medical Imaging*, 16(4):439-446, 1997.

Lichtenstein, "Method and Apparatus for Percutaneous Reduction of Anterior-Posterior Diameter of Mitral Valve," U.S. Appl. No. 10/690,131, filed Oct. 20, 2003, 31 pages.

Mack, "New Techniques for Percutaneous Repair of the Mitral Valve," *Heart Failure Review*, 11:259-268, 2006.

Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.

Sharkey et al., "Left Ventricular Apex Occluder. Description of a Ventricular Partitioning Device," *EuroIntervention* 2:125-127, 2006.

Stiles, et al., "Simulated Characterization of Atherosclerotic Lesions in the Coronary Arteries by Measurement of Bioimpedance," *IEE Transactions on Biomedical Engineering*, 50(7):916-921, 2003.

Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.

Timek et al., "Septal-Lateral Annular Cinching ('SLAC') Reduces Mitral Annular Size Without Perturbing Normal Annular Dynamics," *Journal of Heart Valve Disease* 11(1):2-10, 2002.

Timek et al., "Septal-Lateral Annular Cinching Abolishes Acute Ischemic Mitral Regurgitation," *Journal of Thoracic and Cardiovascular Surgery*, 123(5):881-888, 2002.

Valvano et al., "Thermal Conductivity and Diffusivity of Biomaterials Measured with Self-Heated Thermistors," *International Journal of Thermodynamics*, 6(3):301-311, 1985.

Gelbart et al., "Automatic Atherectomy System," Office Action mailed Mar. 4, 2009 for U.S. Appl. No. 11/436,584, 7 pages.
Gelbart et al., "Automatic Atherectomy System," Amendment filed Aug. 4, 2009 for U.S. Appl. No. 11/436,584, 15 pages.
Gelbart et al., "Automatic Atherectomy System," Office Action mailed Dec. 1, 2009 for U.S. Appl. No. 11/436,584, 10 pages.
Gelbart et al., "Automatic Atherectomy System," Amendment filed Mar. 30, 2010 for U.S. Appl. No. 11/436,584, 20 pages.
Gelbart et al., "Automatic Atherectomy System," Amendment filed Oct. 25, 2010 for U.S. Appl. No. 11/436,584, 9 pages.
Gelbart et al., "Automatic Atherectomy System," Office Action mailed Dec. 14, 2010 for U.S. Appl. No. 11/436,584, 12 pages.
Gelbart et al., "Intra-Cardiac Mapping and Ablation Method," Preliminary Amendment filed Aug. 29, 2007 for U.S. Appl. No. 11/475,950, 42 pages.
Gelbart et al., "Intra-Cardiac Mapping and Ablation Method," Amendment filed Mar. 5, 2008 for U.S. Appl. No. 11/475,950, 11 pages.
Gelbart et al., "Intra-Cardiac Mapping and Ablation Method," Office Action mailed Jun. 23, 2010 for U.S. Appl. No. 11/475,950, 18 pages.
Gelbart et al., "Intra-Cardiac Mapping and Ablation Method," Amendment filed Aug. 16, 2010 for U.S. Appl. No. 11/475,950, 22 pages.
Gelbart et al., "Intra-Cardiac Mapping and Ablation Method," Office Action mailed Nov. 23, 2010 for U.S. Appl. No. 11/475,950, 25 pages.
Gelbart et al., "Intra-Cardiac Mapping and Ablation Method," Amendment filed Feb. 23, 2011 for U.S. Appl. No. 11/475,950, 28 pages.
Gelbart et al., "Medical Device for Use in Bodily Lumens, for Example an Atrium," Office Action mailed Jul. 25, 2011 for U.S. Appl. No. 11/941,819, 9 pages.
International Preliminary Report on Patentability, issued Jan. 6, 2009, for PCT/US2007/014902, 8 pages.
International Search Report, mailed Dec. 5, 2007, for PCT/US2007/014902, 5 pages.
International Search Report, mailed Dec. 2, 2009, for PCT/US2008/083644, 5 pages.
Written Opinion, mailed Dec. 5, 2007, for PCT/US2007/014902, 7 pages.
Written Opinion, mailed Dec. 2, 2009, for PCT/US2008/083644, 9 pages.
Gabriel et al., "The Dielectric Properties of Biological Tissues: I. Literature Survey," Phys. Med. Biol. 41:2231-2249, 1996.
Gelbart et al., "Liposuction System," Office Action mailed Mar. 16, 2011 for U.S. Appl. No. 12/010,458, 12 pages.
Gelbart et al., "Liposuction System," Amendment filed Jun. 10, 2011 for U.S. Appl. No. 12/010,458, 10 pages.

* cited by examiner

AUTOMATIC ATHERECTOMY SYSTEM

CROSS REFERENCE TO RELATED APPLICATIONS

This application is a division of U.S. patent application Ser. No. 11/436,584 filed May 19, 2006, now pending, which is incorporated herein, by reference, in its entirety.

FIELD OF THE INVENTION

This application relates to medical devices and in particular to procedures in which an undesired tissue has to be removed without harming an adjacent desired tissue, such as in atherectomy.

BACKGROUND OF THE INVENTION

In many medical procedures an undesirable tissue is adherent or touching a desired tissue and the removal of the undesired tissue has to be done with extreme caution in order not to harm the desired tissue. A well known example is atherectomy, the process of removing plaque from blood vessels. The most common method of atherectomy is based on the use of a high speed rotary burr, mounted at the end of a very flexible catheter. The burr pulverizes the plaque into such fine particles that they can be left in the blood stream. A well known system is manufactured by the Boston Scientific Company (www.bostonscientific.com) under the name Rotablator™. No further data is given here about this system as it is a well known commercial system. Other potential uses of the invention are removal of tumors, such as prostate cancer, liposuction, dental work and more. Today most of these procedures are performed by a surgeon manipulating a surgical tool (directly or remotely) while observing the tool position using means such as fluoroscopy or ultrasound, or by tactile feel. In some procedures there is no need to remove tissue but there is still a need to navigate within the body, such as directing a catheter through the blood system. The present invention can save the majority of the surgeon's time and operating room expenses.

SUMMARY OF THE INVENTION

The present embodiments of the invention provide an automated way to navigate within the body and remove undesired tissue without doing any harm to desired tissue, even in situations where the undesired tissue is adherent. The same approach can be used for just navigation, without tissue removal. The preferred embodiment shown is atherectomy. In atherectomy there is a need to differentiate between plaque and blood vessel wall. It is well known that plaque has different electrical properties than blood vessel wall; however the blood vessels are full of blood which has electrical properties similar to the vessel wall. In order to automate atherectomy a discriminator between vessel wall, plaque and blood is required. Also, it is desired to sense proximity to a vessel wall, not just contact. The embodiments of the present invention provide exactly this capability. A similar situation exists in some tumor removal procedures: some tumors have different electrical properties than healthy tissue but the in-situ measurement of these properties is complicated by the fact that the voids left in the process of tissue removal are being filled with fluids which affect the measurements. Prior attempts to automate atherectomy relied on a guide wire (which cannot be used in case of complete occlusion) or on devices to help the surgical tool glide in a correct trajectory within the blood vessel. Since the plaque can be softer or harder than the vessel wall, it is very difficult to rely on such "self steering" methods. The approach described herein identifies the different materials surrounding the rotary burr at the tip of the atherectomy catheter and automatically steers the burr to remove the undesired tissue, such as plaque.

The invention uses the tip of a catheter as a sensing device, in order to measure both the electrical conductivity and permittivity of the surrounding tissue at multiple frequencies. From these parameters it is determined which tissue lies in the different directions. A servo system steers the catheter tip in the direction of the tissue to be removed. In non-atherectomy applications the rotary tip can be replaced with any desired tool and the system can be used to automatically steer the catheter to the desired position. The steering is done hydraulically, by pressurizing miniature bellows located near the catheter tip.

In general, the invention can be used for a broad range of applications as the invention does not rely on the type of procedure used. It can be used with rotary burrs, stents, guide wires, suction, electro-surgery etc.

In atherectomy there is a need to differentiate between at least three types of tissue: vessel wall, plaque and blood. Both vessel wall and blood have high conductivity and high permittivity, while plaque has low conductivity and permittivity. The key for differentiating blood from vessel wall is the change in permittivity with frequency: the permittivity of the vessel wall falls much faster as the frequency increases.

Other features and advantages of the invention will become apparent by studying the description of the preferred embodiment in conjunction with the drawings.

DETAILED DESCRIPTION OF THE INVENTION

Figure 1:
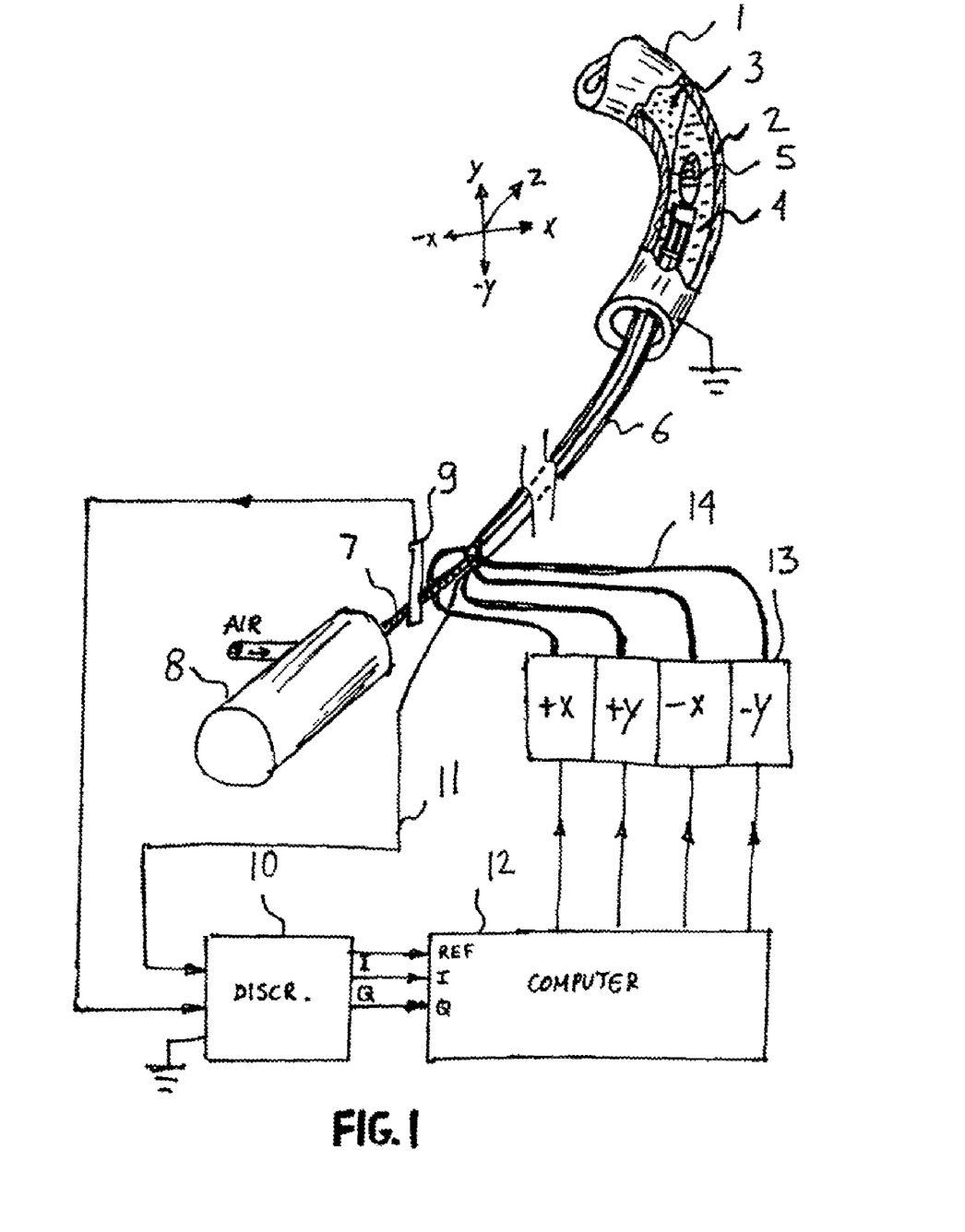
FIG. 1 is a schematic view of according to one illustrated embodiment.

Referring to FIG. 1, a blood vessel 1 having a wall 2 contains undesired plaque 3 as well as blood 4. An atherectomy tool 5 is introduced using catheter tube 6. The tool is driven by air motor 8 via flexible rotating cable 7. No further details of the atherectomy system are given, as these are well known commercial systems such as the Rotablator™ system. An electrical contact 9 measures the electrical impedance between cable 7 and the return path which is ground (the patient is electrically grounded). The discriminator 10 measures the complex impedance to ground by measuring the In-Phase current (I) and the Quadrature, or 90 deg out of phase current (Q). From these measurements the conductivity and permittivity of the tissue can be computed, based on the well known methods of electrical impedance measurements. A full explanation is given later. Based on the measured value, the type of tissue is determined by computer 12 and the catheter is automatically steered by hydraulic actuator 13 (via tubes 14) to remove the undesired plaque 3. As it approaches the wall 2, the electrical properties start changing allowing precise and gentle steering and removal up to the wall 2 but without actually touching the wall. This is possible as the measured properties are also a function of tissue thickness, so when the plaque becomes very thin the properties of the underlying layer are showing through. In order to determine the rotational orientation of burr 5 a sense wire 11 is used in conjunction of a conductive strip on burr 5.

Figure 2:
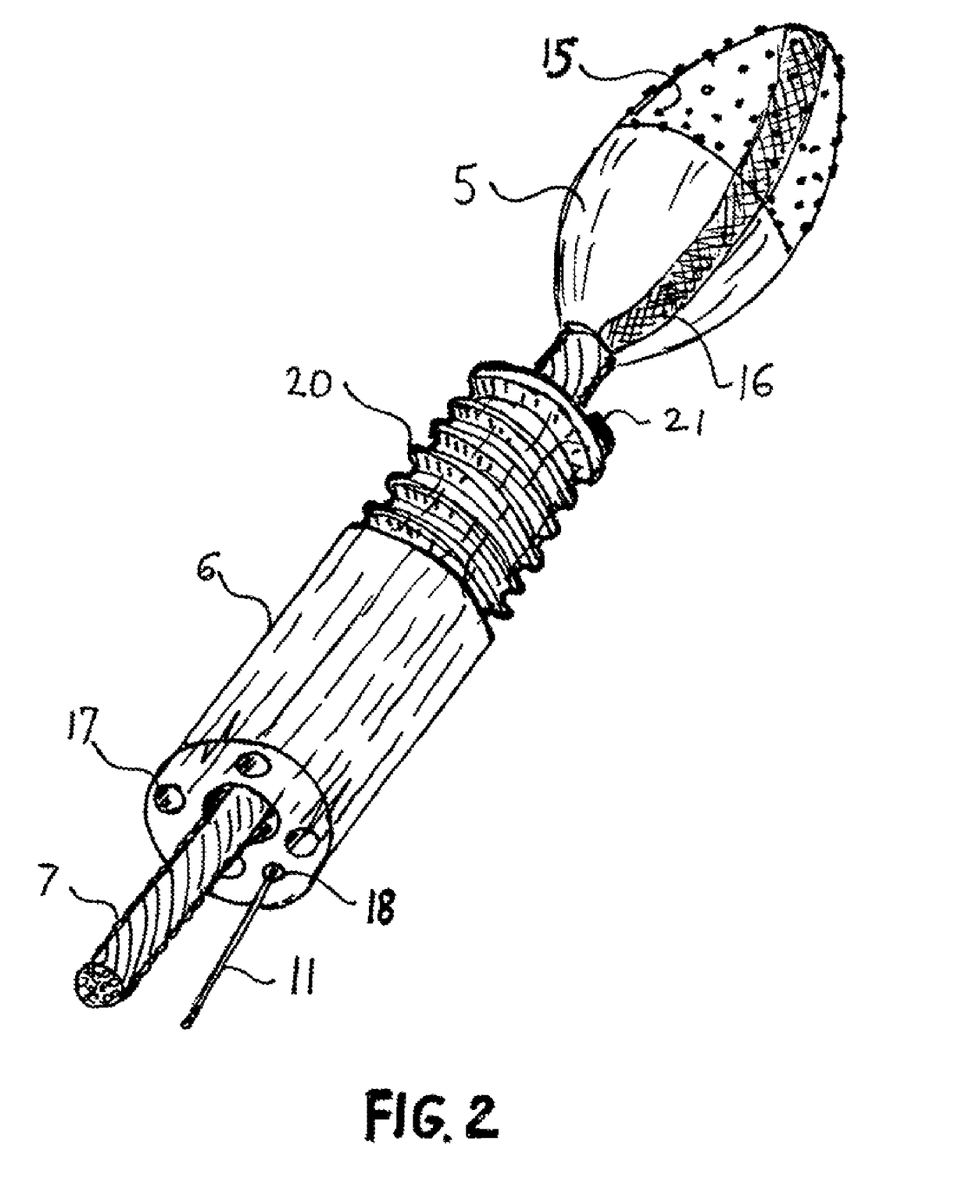
FIG. 2 is an isometric close-up view of the catheter tip.
Figure 3:
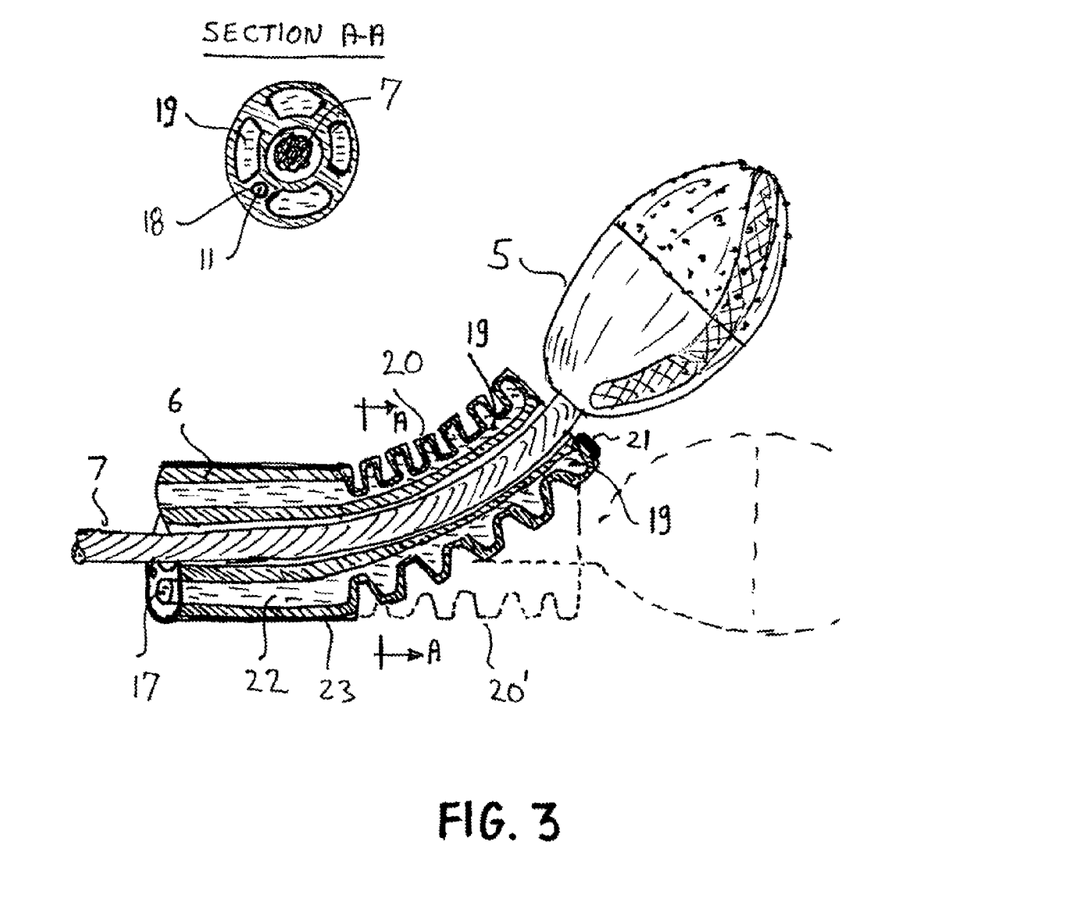
FIG. 3 is a cross section of the catheter tip showing the steering method.

Referring now to FIG. 2, the rotary burr 5 has a standard diamond powder coating 15 and is rotated at high speed by cable 7. It is made from electrically insulating material such as ceramic, with the exception of metallized strip 16. Alternatively, it can be made of metal and coated with a hard ceramic coating except for strip 16. A sense wire 11 terminates with tip 21 very close to burr 5. Once per rotation strip 16 comes close to tip 21. This point can be detected by measuring the electrical impedance between wire 11 and cable 7. A sharp drop signifies this point, which is used as a rotational reference point. Catheter 6 contains five channels on top of the central channel used by cable 7. Channel 18 is used for sense wire 11. Channels 17 are used to steer burr 5 in the desired direction by inflating sections of bellows 20. Referring now to FIG. 3, bellows 20 is divided into four separate sections 19 connected to channels 17. Pressurizing a section will cause it to elongate, bending bellows 20 in the opposite direction. Fluid 22 is a saline solution or pure water. For lower electrical noise the outside of catheter 6 is metallized with a very thin coating 23. A sub-micron thickness, deposited by sputtering or evaporation, is sufficient. Such a thin coat does not affect flexibility.

Figure 4:
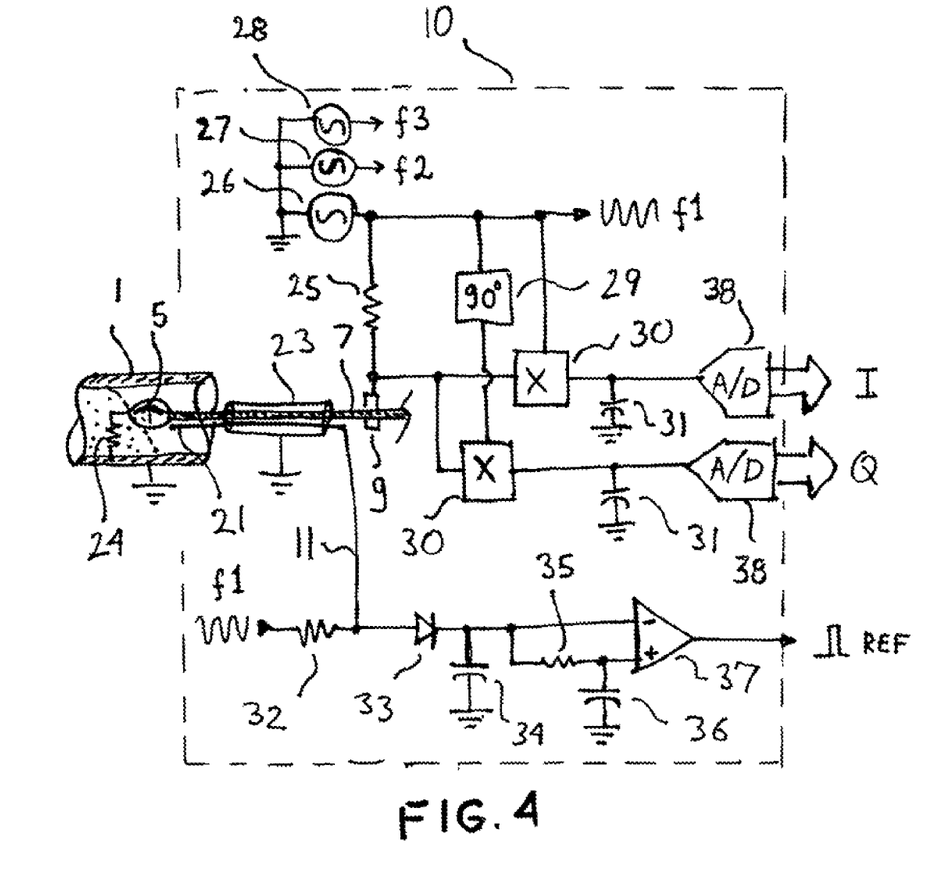
FIG. 4 is a schematic diagram of the tissue discriminator.

The discrimination of tissue types is shown in FIG. 4. To discriminate plaque from the wall of a blood vessel by electrical properties is relatively easy and well known in the medical literature, as plaque has a higher electrical impedance (both lower conductivity and lower permittivity). It is more difficult to differentiate the wall from the blood filling the vessel, as both have high conductivity and high permittivity. However, the permittivity of the wall falls much faster (by about a factor of 1000 faster) with frequency. This can be seen from the following table. While the cited values differ between studies, all studies show that permittivity of blood falls much slower than permittivity of the vessel wall as frequency increases.

| | $\log_{10}(\text{Freq})$ | | | | |
|---|---|---|---|---|---|
| | 3 | 5 | 6 | 7 | 8 |
| | Conductivity (S/m) | | | | |
| Blood | 0.70 | 0.70 | 0.70 | 1.00 | 1.49 |
| Fat | 0.025 | 0.025 | 0.030 | 0.040 | 0.060 |
| Muscle | 0.40 | 0.40 | 0.40 | 0.40 | 0.75 |
| Fibrous Material | 0.24 | 0.24 | 0.24 | 0.29 | 0.33 |
| Calcium | 0.08 | 0.08 | 0.10 | 0.12 | 0.17 |
| Vessel Wall | 0.58 | 0.58 | 0.58 | 0.67 | 0.83 |
| | Relative Permittivity | | | | |
| Blood | 4100 | 4000 | 2000 | 300 | 75 |
| Fat | 20000 | 100 | 50 | 30 | 12 |
| Muscle | 400000 | 10000 | 8000 | 200 | 70 |
| Fibrous Material | 2000 | 500 | 50 | 5 | 3 |
| Calcium | 10500 | 500 | 250 | 70 | 30 |
| Vessel Wall | 100000 | 5000 | 4000 | 100 | 30 |

The impedance of the tissue to ground (the patient is grounded) is shown schematically as impedance 24. A current is sent from oscillator 26 via resistor 25, contact 7, cable 7 and burr 5 to the tissue impedance 24. The lower the impedance 24 the lower the voltage at contact 9 will be. Both the in-phase component I and the quadrature component Q is measured by any one of the standard methods of AC impedance measurement. By the way of example, the I component is found by multiplying output f1 of oscillator 26 with the voltage senses at contact 9 using an analog multiplier 30. The Q component is found by multiplying the same voltage with the output of f1 shifted by 90 degrees by phase shifter 29. The output of the multipliers are filtered by capacitors 31 and converted to digital by A/D converters 38. This is the standard sine and cosine separation method for finding the conductivity and permittivity components of a complex impedance. For frequencies below a few MHz, the voltage at contact 9 can be digitized and the derivation of the conductivity and permittivity can be done completely via digital signal processing. In order to generate the rotational reference pulse, the point when the voltage of sense wire 11 drops each revolution has to be found. The actual voltage can vary over a wide range, depending on the surrounding tissue, but the dip is always when the conductive strip 16 (see FIG. 2) is nearest to tip 21. By comparing the average voltage at wire 11 to the instantaneous voltage, the reference point is found independent of voltage. Signal f1 is fed to sense wire 11 via resistor 32. The sine wave envelope is detected by diode 33 and capacitor 34. The average is derived by resistor 35 and capacitor 36. Comparator 37 generates a positive output when the instantaneous value is below the average value. Again, the reference pulse generation can also be digital if the signal on wire 11 is digitized from the start.

Since the rate of change of the permittivity with frequency is required, at least two frequencies have to be used, three would be even more accurate. These are generated by oscillators 26, 27 and 28. For each frequency the circuit shown has to be replicated. It is also possible to use a single variable frequency source and single detection circuit and multiplex the detection process.

Figure 5:
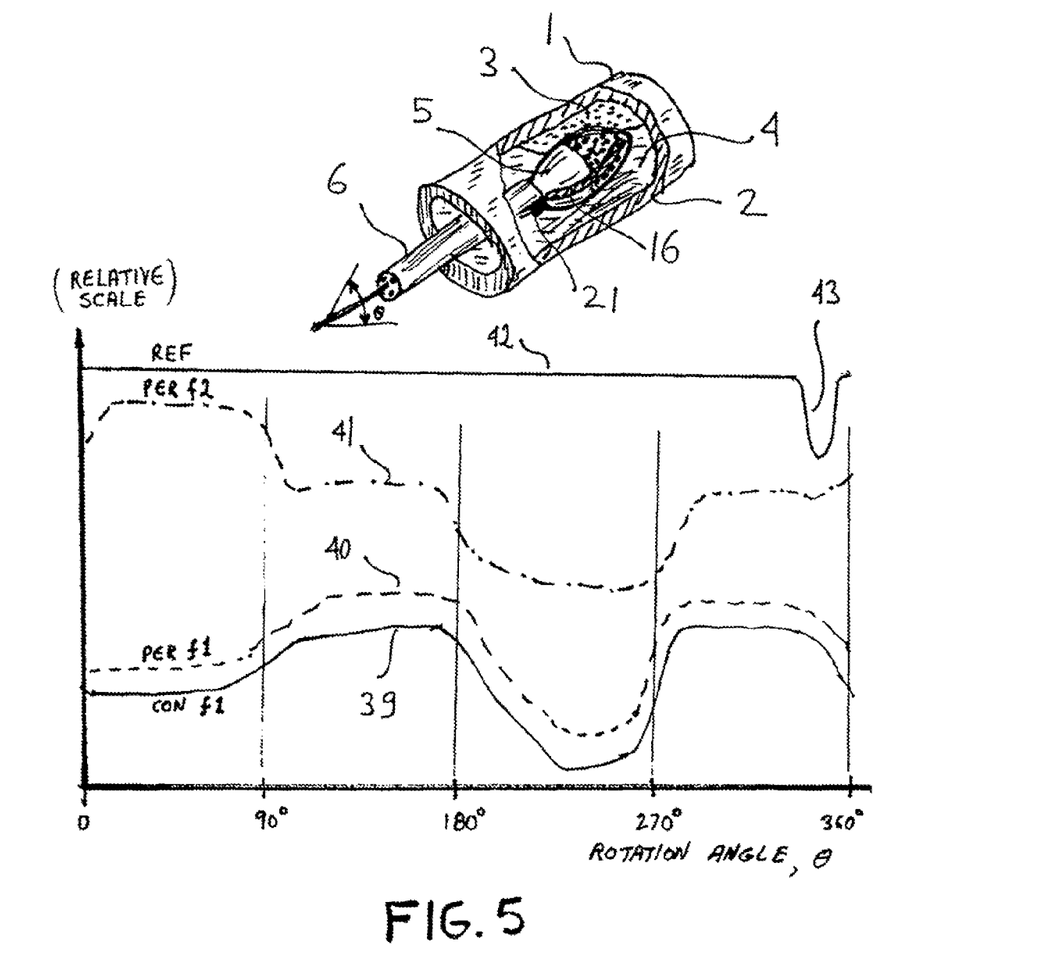
FIG. 5 is a graph of the different waveforms produced by the discriminator.
Figure 7:
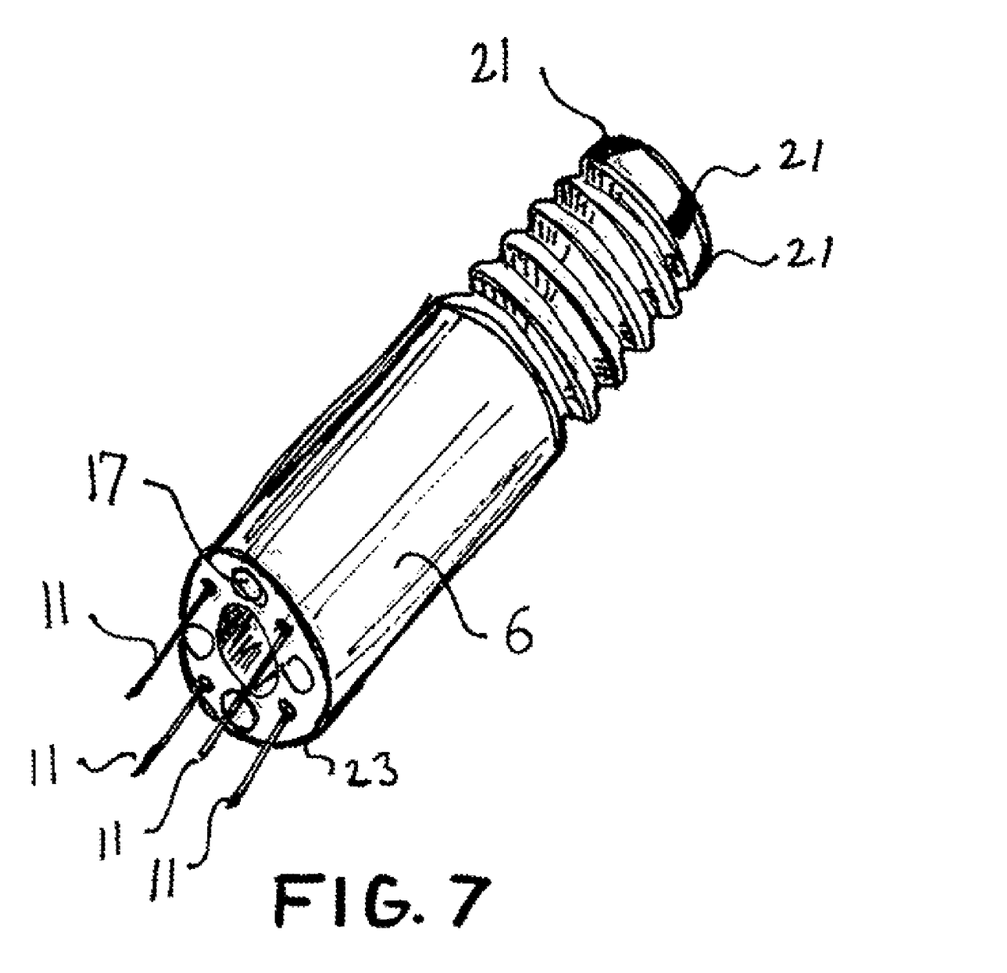
FIG. 7 is an isometric view of an alternate sensing method.

A typical discriminator output is shown in FIG. 5. Graph 43 is the amplitude of the sinewave at sense wire 11, used to generate the rotational reference. Graph 39 shows the conductivity, derived from the I component (the higher the conductivity the lower the I component will be). Graph 40 shows the permittivity, derived from the Q component (the higher the permittivity the lower the Q component will be). Graph 41 shows the permittivity at a much lower frequency. The horizontal scale is in degrees relative to the reference pulse, which is created when tip 21 is nearest to conductive strip 16. In this example tip 21 is drawn close to the vessel wall. Using just the data at f1, it is difficult to tell the wall (0-90 degree range) from blood (above and below burr 5, at 90-180 degree range and 270-360 degree range). At the second frequency f2, the permittivity in the wall area increases much faster than in the blood area. The plaque is easy to spot as it has much lower conductance and permittivity. Using the values of table 1 for frequencies of 1 KHz and 10 MHz, the conductivity and permittivity of plaque (fat+calcium+fibrous material) are below 0.1 S/m and 50, while blood is above 0.7 S/m at both frequencies and wall is above 0.58 at both frequencies. The permittivity of the wall is much higher than blood at 1 KHz (100,000 vs. 4100) but falls much faster at 10 MHz, dropping a factor of 1000 for the wall but only a factor of 14 for blood. This example shows that by using just three factors: conductivity, permittivity and ratio of permittivity at 10 MHz to 1 KHz the three tissues can be discriminated with a large margin. Adding a third frequency f3 increases the accuracy. Note that the rotational speed of the burr 5 is about 1-3 KHz. For oscillator frequencies below that, the results will have to be sampled and integrated over many rotations. This is not a problem, as the steering is done at a much lower bandwidth than the measuring. An alternative is to use a frequency of about 100 KHz as the lowest oscillator frequency. A second alternative, shown in FIG. 7, is to replace the rotary tissue sensing by four sense wires 11 instead of a single one, and have each one connect to a discriminator. Each one of the wires corresponds to one actuator direction. The advantages are:

1. A completely standard burr can be used, however sensing does not extend tip of burr.
2. System can be used for applications not requiring rotary burrs.
3. Only low frequency processing is required, as processing can be done at the steering bandwidth instead of the rotation speed. Steering bandwidth is below 100 Hz.

The catheter has four actuation channels 17 and four sense wires 11 terminating in four tips 21. If a burr is used, tips can protrude to partially envelope burr.

The computer 12 in FIG. 1 performs the discrimination between tissues based on the rules shown above and steers the burr 5 into the undesired tissue, in this case plaque. Clearly the decision rules and parameters will change with the application and the tissue used. A large data base of impedance data for a large number of tissues is posted on the Italian National Research Council website at: http://niremf.ifac.cn-r.it/cgi-bin/tissprop/htmlclie/uniquery There are similar data bases available on the internet for properties of malignant tumors versus healthy tissue.

Figure 6:
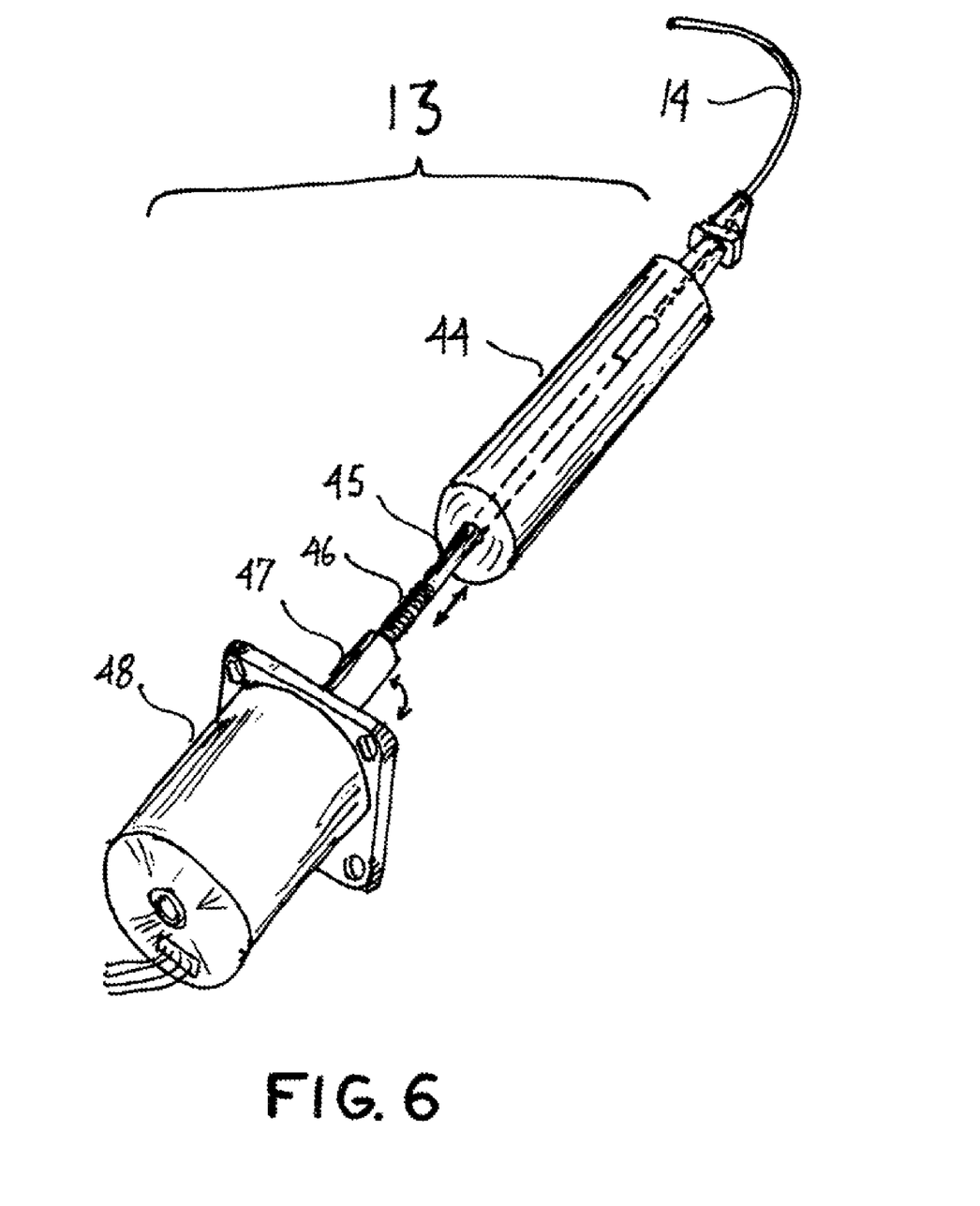
FIG. 6 is an isometric view of the actuation mechanism.

The hydraulic actuators 13 are shown in FIG. 6 in conjunction with FIG. 1. A motor, such as a stepper motor, 48 is driven from computer 12 via a standard interface. A piston 45 is moved in a cylinder 44 via the action of a thread 46 and a mating female thread 47. The pressure is transmitted via hypodermic tubing 14 to channel 17 (not shown) in catheter 6. Four identical units are used for +X, −X, +Y and −Y.

By the way of example, burr 5 is a standard burr with an external diameter of between 1.5 to 2.5 mm. Because the system is automated a single small burr can be used for all blood vessel sizes, as the computer will steer the bar in all radial directions to clean a large vessel. Catheter 6 is slightly smaller than burr 5. Diameter of piston 45 is 1-2 mm and stroke is about 10 mm. Piston 45 and cylinder 44 are made of very hard material, such as alumina, ruby or tungsten carbide, with a lapped fit. The pressure of the fluid is fairly high, typically 50-100 Kg/cm2. Typical component values for the discriminator 10 are: frequencies in the 1 KHz to 1 GHz range, time constants of filter 31 of about 10-100 uS, time constant of capacitor 34 of 10-100 uS, time constant of capacitor 36 and resistor 35 of 10-100 mS.

An alternate way of steering is by using push-wires in channels instead of a liquid. The actuators and catheter are very similar to the ones discussed earlier.

Still another way of steering is use to catheter tips made of ferromagnetic material and have a controlled external magnetic field. A variation is a system having a fixed external field and a catheter tip carrying three orthogonal coils to generate a force in any desired direction. This is available as a commercial system under the trademark Niobe. It is sold by the Stereotaxis corporation (vwww.stereotaxis.com).

While the preferred embodiment relates to atherectomy and used electrical impedance sensing other applications and other sensing methods are part of this invention. By the way of example, different tissues can be discriminated by their mechanical properties such as stiffness, hardness and damping. This can be sensed by a vibrating tip. Tissues can also be discriminated by thermal properties. A tip similar to FIG. 7 can carry four temperature dependent resistors instead of sensing tips 21. A constant current is passed through resistors and their temperature is measured by the voltage drop across them. Different tissues have different heat conductivities: plaque will conduct less than blood vessel wall while blood will conduct heat rapidly, as convection exists.

Also, the word "automatically" in this disclosure and claims should be broadly interpreted, from a simple assist to the surgeon in operating surgical systems to fully unattended operation of such a system. In the minimal version the surgeon fully controls the system; the tissue discriminator just assists the surgeon in the decision and operation of the atherectomy or other system. In a fully unattended operation the catheter can also be automatically advanced into the body and can be programmed to enter the correct blood vessel when coming to a junction point where there are multiple choices of routes. In the same manner, the "tool" or "catheter tip" should be broadly interpreted to include both contact tools (burrs, rotary wires, blades, suction, electro-surgery etc) as well as non contact tools (lasers, water-jet, gas jet etc).

The invention claimed is:

1. A tissue removal system, comprising:
a cutting tool coupleable to a catheter to be percutaneously positioned within a body cavity, the cutting tool rotatable with respect to the catheter and operable to remove an undesired tissue from a desired tissue in the body cavity, the cutting tool responsive to at least one physical characteristic of at least two different types of tissue;
a rotary drive subsystem drivingly coupleable to the cutting tool to selectively cause the cutting tool to rotate within the body cavity;
a discrimination subsystem communicatively coupled to the cutting tool to receive signals therefrom indicative of a plurality of electrical characteristics of tissue to which the cutting tool is at least proximate, determined at a plurality of frequencies, the discrimination subsystem configured to discriminate between at least the two different types of tissue based on the plurality of electrical characteristics determined at the plurality of frequencies indicated by the signals received from the cutting tool;
a computer communicatively coupled to the discrimination subsystem to receive signals therefrom indicative of one or more tissue types and configured to determine a direction of travel for the rotary cutting tool based at least in part on the signals indicative of the one or more tissue types; and
a steering mechanism communicatively coupled to the computer and physically coupleable to the catheter, and configured to control a direction of travel of the rotary cutting tool in response to the direction of travel determined by the computer.

2. The tissue removal system of claim 1 wherein the cutting tool is a burr.

3. The tissue removal system of claim 1 wherein the cutting tool comprises an electrically insulative body and at least one electrically conductive strip extending along an outer surface of the electrically insulative body.

4. The tissue removal system of claim 3 wherein the discrimination subsystem includes a sense line having a tip positioned sufficiently proximate the cutting tool to detect a passage of the electrically conductive strip once each revolution of the cutting tool.

5. The tissue removal system of claim 3 wherein the discrimination subsystem further includes a discrimination circuit that discriminates between plaque, blood vessel walls and blood based on the signals received from the cutting tool.

6. A tissue removal system, comprising:

a cutting tool coupleable to a catheter to be percutaneously positioned within a body cavity, the cutting tool rotatable with respect to the catheter and operable to remove an undesired tissue from a desired tissue in the body cavity, the cutting tool responsive to at least one physical characteristic of at least two different types of tissue;

a rotary drive subsystem drivingly coupleable to the cutting tool to selectively cause the cutting tool to rotate within the body cavity;

a discrimination subsystem communicatively coupled to the cutting tool to receive signals therefrom indicative of at least one electrical characteristic of tissue to which the cutting tool is at least proximate, determined at a plurality of frequencies, the discrimination subsystem configured to discriminate between at least the two different types of tissue based on the at least one electrical characteristic determined at the plurality of frequencies indicated by the signals received from the cutting tool;

a steering mechanism physically coupleable to the catheter and configured to control a direction of travel of the rotary cutting tool, wherein the steering mechanism comprises a bellows shaped coupler that has a central channel and a plurality of longitudinally extending hollow sections spaced radially about the central channel.

7. The tissue removal system of claim 6 wherein the steering mechanism further comprises a source of fluid under pressure fluidly coupleable to the bellows shaped coupler to selectively pressurize selected ones of the hollow sections thereof.

8. The tissue removal system of claim 7 wherein the steering mechanism further comprises a computer configured to control a pressure applied to each of the hollow sections of the bellows shaped coupler.

9. The tissue removal system of claim 8 wherein the computer is configured to automatically control the pressure applied to each of the hollow sections of the bellows shaped coupler based at least in part on the signals received by the discrimination subsystem from the cutting tool.

* * * * *

UNITED STATES PATENT AND TRADEMARK OFFICE
CERTIFICATE OF CORRECTION

| | |
|---|---|
| PATENT NO. | : 8,150,499 B2 |
| APPLICATION NO. | : 12/950871 |
| DATED | : April 3, 2012 |
| INVENTOR(S) | : Daniel Gelbart et al. |

It is certified that error appears in the above-identified patent and that said Letters Patent is hereby corrected as shown below:

Item (75):
"Daniel Gelbart, Vancouver (CA); Samuel Victor Lichtenstein, Vancouver (CA)" should read,
--Daniel Gelbart, Vancouver, BC (CA); Samuel Victor Lichtenstein, Vancouver, BC (CA)--.

Item (73):
"Kardium Inc., Vancouver (CA)" should read, --Kardium Inc., Vancouver, BC (CA)--.

Signed and Sealed this
Seventeenth Day of July, 2012

David J. Kappos
*Director of the United States Patent and Trademark Office*